(12) United States Patent
Adel et al.

(10) Patent No.: US 7,804,863 B2
(45) Date of Patent: Sep. 28, 2010

(54) LASER SYSTEM

(75) Inventors: Peter Adel, Munich (DE); Marc Fischer, Munich (DE); Michael Mei, Munich (DE); Ronald Holzwarth, Munich (DE)

(73) Assignee: Menlo Systems GmbH, Martinsried (DE)

( * ) Notice: Subject to any disclaimer, the term of this patent is extended or adjusted under 35 U.S.C. 154(b) by 249 days.

(21) Appl. No.: 11/804,694

(22) Filed: May 18, 2007

(65) Prior Publication Data

US 2008/0069159 A1    Mar. 20, 2008

(30) Foreign Application Priority Data

May 19, 2006  (DE) ................... 10 2006 023 601

(51) Int. Cl.
*H01S 3/30* (2006.01)
(52) U.S. Cl. ............... 372/3; 372/6; 372/18; 372/28; 359/326; 359/327; 359/333; 359/334
(58) Field of Classification Search ............ 372/3, 372/6, 18, 28; 359/326, 327, 333, 334
See application file for complete search history.

(56) References Cited

U.S. PATENT DOCUMENTS

| | | | | |
|---|---|---|---|---|
| 5,754,334 A * | 5/1998 | Artiglia et al. ............. 359/332 |
| 6,501,594 B1 * | 12/2002 | Hwang et al. ............ 359/341.32 |
| 6,724,788 B1 * | 4/2004 | Holzwarth et al. ............ 372/32 |
| 6,744,553 B1 * | 6/2004 | Islam et al. ............... 359/326 |
| 6,813,429 B2 * | 11/2004 | Price et al. ................ 385/125 |
| 6,870,663 B2 * | 3/2005 | Kato et al. ................ 359/326 |
| 6,885,683 B1 * | 4/2005 | Fermann et al. ............. 372/25 |
| 7,187,864 B2 * | 3/2007 | Haensch et al. .............. 398/43 |
| 2002/0044339 A1 | 4/2002 | Chesnoy et al. |
| 2003/0035202 A1 * | 2/2003 | Islam et al. ................ 359/334 |
| 2003/0043451 A1 | 3/2003 | Kato et al. |
| 2003/0053192 A1 * | 3/2003 | Islam et al. ................ 359/327 |
| 2006/0045540 A1 * | 3/2006 | Sato et al. ................. 398/176 |
| 2006/0245461 A1 * | 11/2006 | Islam ....................... 372/75 |

OTHER PUBLICATIONS

Kobtsev et al., "Coherent Properties of Super-Continuum Containing Clearly Defined Solitons", Optics Express, vol. 14, No. 9, May 1, 2006, pp. 3968-3980.
Mitschke et al., "Discovery of the Soliton Self-Frequency Shift", Optics Letters, vol. 11, No. 10, Oct. 1986, pp. 659-661.

* cited by examiner

*Primary Examiner*—Minsun Harvey
*Assistant Examiner*—Yuanda Zhang
(74) *Attorney, Agent, or Firm*—Flynn, Thiel, Boutell & Tanis, P.C.

(57) ABSTRACT

The invention concerns a laser system with a frequency comb generator for generating a comb of optical frequencies having an offset frequency and a plurality of equidistant modes. The laser system further preferably includes at least one stabilizer for stabilizing the frequency comb onto a certain offset frequency and/or onto a certain mode spacing. The laser system further includes an optical amplifier for amplifying the frequency comb coupled out of the frequency comb generator, the amplification factor of this amplifier being variable; and the amplifier is followed by a Raman medium for generating a Raman shift of the frequency comb.

35 Claims, 2 Drawing Sheets

LASER SYSTEM

BACKGROUND OF THE INVENTION

1. Field of the Invention

Figure 1:
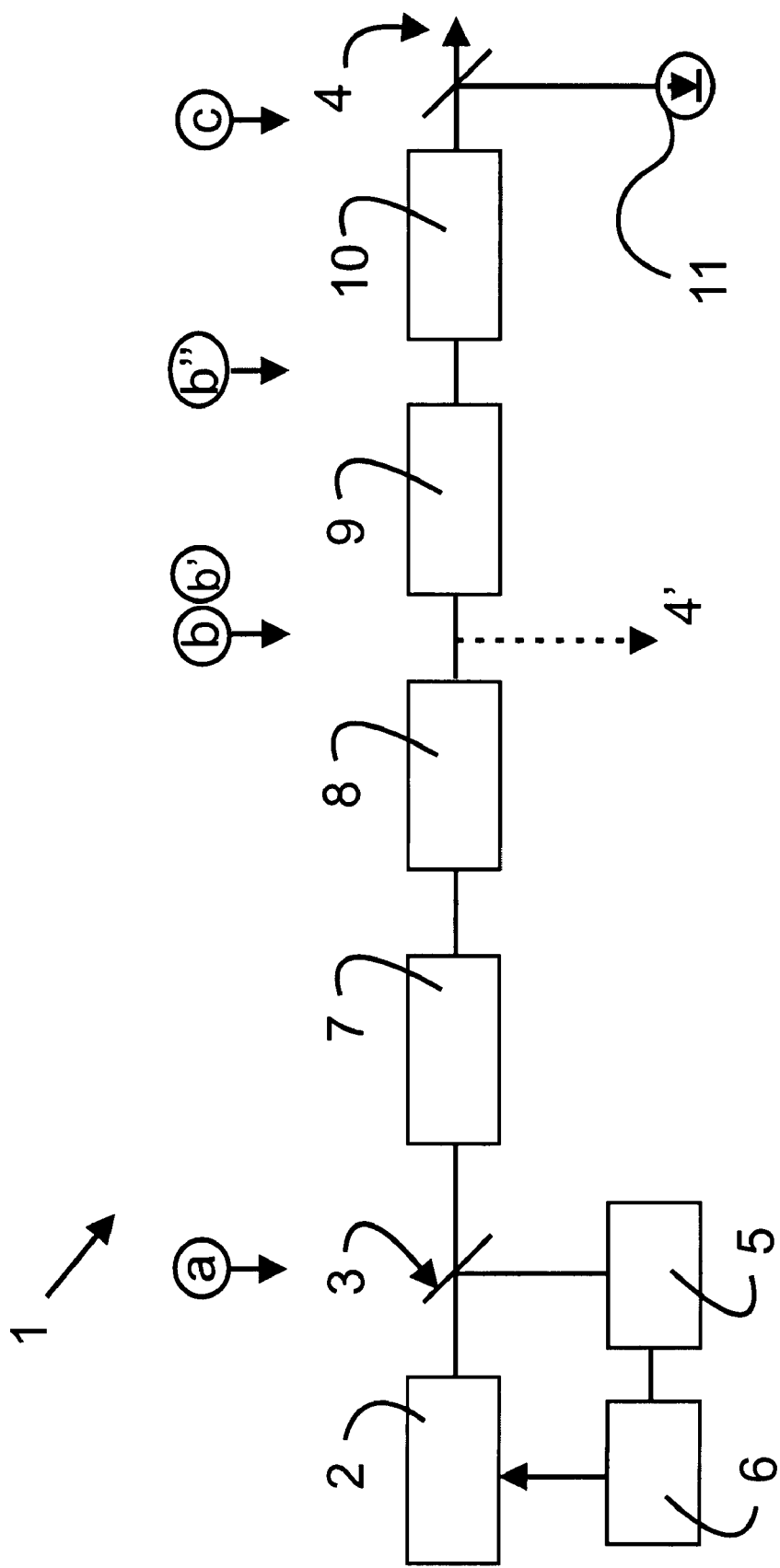

The present invention is directed to a laser system with a frequency comb generator for generating a frequency comb of optical frequencies with an offset frequency and a plurality of equidistant modes.

2. Prior Art

Such a laser system comprises as an important component a frequency generator as known from DE 199 11 193 A1, the corresponding EP 1 161 782 B1 or DE 100 44 404 C2. In each of these conventional systems, a short pulse or ultra short pulse oscillator is provided as the frequency comb, i.e. a mode locked laser with pulse durations in the range from femtoseconds (fs) to nanoseconds (ns). When performing a Fourier transformation from the time domain into the frequency domain, the sequence of laser pulses corresponds to a "frequency comb" in the frequency domain. This comb is constituted by a plurality of sharp δ-like functions at different discrete frequencies, called modes $f_n$. Adjacent modes have a mutual distance or spacing $\Delta f$ from each other which corresponds exactly to the pulse repetition rate of the oscillator and which is therefore determined by the optical path length of the pulses within the oscillator.

However, under normal conditions the modes of the frequency comb are not located exactly at an integer multiple of $\Delta f$, but the whole frequency comb is shifted by a so-called offset frequency $f_0$. Hence, the frequency comb may mathematically be described as $f_n = f_0 + n \Delta f$. The offset frequency $f_0$ stems from the circumstance that the group velocity for the pulses trapped in the oscillator, which governs the repetition rate and thereby the mode spacing $\Delta f$, is different from the phase velocity of the single modes.

DE 199 11 193 A1, EP 1 161 782 B1, and DE 100 44 404 C2 describe methods by which the two degrees of freedom of the frequency comb, i.e. the offset frequency $f_0$ and the mode distance $\Delta f$, may be set and controlled to fixed, predetermined values. For this purpose, a stabilizer or feedback circuit is provided for each degree of freedom. A first stabilizer concerns the mode spacing. The input value for this stabilizer may be the pulse repetition rate (if necessary, divided or multiplied into more easily accessible ranges), which corresponds to the mode spacing. An interpreting and comparing unit compares the measured value with a predetermined reference value of the pulse repetition rate. In order to control or vary the mode spacing or in order to fix the value at a measured deviation onto a predetermined reference value, the stabilizer controls an actuator that may vary the optical path length of the oscillator and, thus, the pulse repetition rate. For example, the actuator may be a linear drive or a piezo actuator for a resonator mirror of the oscillator.

A second stabilizer controls the offset frequency $f_0$ onto a predetermined value. For this purpose, for example, a selected mode $f_n$ of the frequency comb is superposed on a detector (e.g. a photodiode or a photo multiplier) with either an external, exactly known reference frequency (e.g. from a continuous wave laser) or with a frequency converted, second mode of the same frequency comb. The superposition on the detector generates a beat frequency in the radio frequency range. An interpretation and comparison unit compares the beat frequency with a predetermined, where appropriate variably selectable reference frequency. If a deviation is detected, the second stabilizer controls an actuator that varies the linear dispersion within the oscillator. For example, this can be achieved by slightly inclining a resonator end mirror in a branch of the resonator that is passed by the spatially separated modes, in order to change the optical path length of the oscillator in dependency on frequency. Alternatively, the pump power for the oscillator may be varied, or a dispersive element like a pair of prisms or a transparent, tiltable plate may be introduced into the optical path of the oscillator and varied in its position.

With the means described in DE 199 11 193 A1, EP 1 161 782 B1, or DE 100 44 404 C2, a completely stabilized frequency comb can be generated, the single modes of which are located at exactly determined frequencies and are mutually coherent. Concerning the detailed description of these means, attention is drawn to the three preceding documents, the entire content of which is herein incorporated by reference.

The coherence of the frequency comb is of particular importance. In other words, there should be a fixed phase frequency between the single modes of the frequency comb. This coherence is not present, for example, when using Q-switched lasers. Further, a plurality of non-linear optical processes is known in fibers which lead to a loss of coherence properties.

The stabilized frequency comb has properties that allow a plurality of unique applications. Since the position of its modes is fixed with absolute certainty in the frequency domain, single modes may be used as a frequency standard or for the exact measurement of an unknown, external optical frequency. Also, it is possible to use single or several modes for spectroscopy.

However, the range of applications of a stabilized frequency comb is limited by the fact that only a limited number of modes exceed a certain amplitude level. These modes are determined by the laser medium of the oscillator. For example, if a fiber laser with an erbium doped fiber is taken as the oscillator, its central output wavelength is located at approximately 1550 nm. The shorter the pulses that are output from the oscillator, the larger is their spectral width. With fs pulses, the full width at half maximum of the spectrum may have a range of several ten nm up to several 100 nm with sub-10-fs pulses.

It would be extremely interesting to have a stabilized frequency comb with its full coherence properties not only at 1550 nm, but also at the largest possible bandwidth of other frequency ranges with a high spectral power density, in order to be able to conduct exact frequency measurements or spectroscopy experiments also in these other frequency ranges.

Methods for varying the central wavelength of short laser pulses are known from EP 1 118 904 A1 or U.S. Pat. No. 6,014,248. However, none of these documents is related to a frequency comb. If with the non-linear processes described in these documents the coherence properties of the comb and/or the information on the offset property are lost, the position of the modes would not be known anymore, such that the frequency comb would be useless for high precision measurements. However, the knowledge of the exact position of a mode is aimed at neither in EP 1 118 904 A1, nor in U.S. Pat. No. 6,014,249.

A while ago, a first method for transferring a stabilized frequency comb from the infrared into the visible spectral range was suggested. In this method, the frequency of the stabilized frequency comb modes obtained from the oscillator are doubled in a frequency doubling crystal, such that the central wavelength is shifted from 1560 nm to 780 nm. Subsequently, the frequency comb passes a photonic crystal fiber (PCF, also known as microstructured fiber) that broadens the frequency comb over more than an octave. Hence, after passing the fiber the comb comprises a frequency f and also the double frequency 2f. However, during the spectral broadening the average power of the frequency comb is decreased, for example from 100 mW to 50 mW. Further, this decreased power is now distributed onto a rather broad spectral range of up to 400 or 500 nm. The spectral power density, i.e. the power for a single wavelength or frequency, furthermore exhibits a distinct profile and, hence, at certain positions is so low that a measurement of an unknown external reference frequency is not possible anymore.

US 2005/0238070 A1 describes the use of optical parametric amplification (OPA) for generating ultrashort pulses at various wavelengths between 900 nm and 2100 nm. However, there is no stabilization of certain modes.

With the device of US 2004/0213302 A1, a continuum shall be generated from a frequency comb by means of a nonlinear fiber, with Raman effects being declared as undesired. Similarly, US 2004/0057682 A1 describes the possibility of continuum generation from a frequency comb. A "Raman shift" is mentioned, but the document does not explain how the mode stability of the frequency comb is affected during continuum generation.

Finally, DE 10 2004 009 068 A1 claims that the comb structure of a frequency comb is not lost during extreme nonlinear optical effects in a fiber. However, this general statement is not helpful as it is known that there are a number of nonlinear effects in optical fibers which destroy coherence, such as modulation instability or Brillouin scattering, for example.

Therefore, it is the object of the present invention to provide a laser system by which a frequency comb is transferable onto different frequencies while fully maintaining its coherence properties and having a sufficiently high power. It might be particularly interesting if the transfer to different frequencies is tunable.

SUMMARY OF THE INVENTION

This object is solved by a laser system of the present invention. Advantageous embodiments of the invention are also disclosed herein.

According to the invention, the laser system of the present invention is characterized by comprising an optical amplifier for amplifying the frequency comb obtained from the frequency generator, by having a variable amplification factor of the amplifier, and by the amplifier being followed by a Raman medium for generating a Raman shift of the frequency comb. Much to the surprise of the inventors, corresponding experiments have shown that an optical amplifier and a Raman medium do not have a negative influence on the coherence properties of the frequency comb. This could not be expected in particular with respect to the Raman medium, since the Raman shift is an "inelastic"diffusion of light, curing which the coherence of the modes or the information of the offset frequency could easily have been lost. Moreover, there are other, non-linear optical effects in optical fibers from which it is known that they destroy the coherence, such as modulation instability or Brillouin scattering.

By means of the Raman shift the laser system of the present invention may successfully shift the frequency comb onto different frequency ranges. Depending on choice and configuration of the Raman medium, the Raman shift may be a Stokes process, during which the modes of the comb are shifted to lower frequencies, or an anti-Stokes process, at which the modes of the comb are shifted to higher frequency.

A significant advantage of the laser system of the present invention is the circumstance that it may make use of the "soliton self-frequency shift" described in "Discovery of the Soliton Self-Frequency Shift," Mitschke and Mollenauer, Optics Letters, vol. 11, no. 10, 1986. The Raman medium of the laser system of the present invention is configured to favor the "soliton self-frequency shift" by favoring the generation of a soliton within the Raman medium, the high peak power of the soliton, in turn, favoring a "soliton self-frequency shift".

In the "soliton self-frequency shift" process, the magnitude of the Raman shift is proportional to or depends on the power of the laser pulses entering into the Raman medium. In the system of the present invention, the amplifier allows for a variation of its amplification factor. The higher the amplification factor, the larger is the subsequent Raman shift. Hence, by controlling the amplification factor of the amplifier, the position of the maximum of the frequency comb is tunable continuously and in a simple way, and the position of the maximum may be set rapidly and precisely. The amplifier has the additional advantage of increasing the power of the output radiation. Furthermore, the frequency shift is achieved without an enormous spectral broadening, such as in a photonic crystal fiber. Therefore, the output of the present laser system provides a frequency comb with a very high spectral power density that is ideally suited for high precision, low noise frequency measurement. This is a significant advantage if tunable cw laser sources are to be measured with high precision.

In first experiments in connection with the present invention, a diode laser pumped fiber laser with an erbium doped fiber and a central wavelength of approximately 1560 nm was used as a frequency comb. By means of an optical amplifier and a subsequent Raman medium, the central wavelength of the frequency comb could be shifted under full preservation of the coherence properties from approximately 1550 nm up to 2.0 micrometers, and even further to 2.2 micrometers, i.e. by more than 40%. Towards higher wavelengths, the magnitude of the Raman shift obviously is merely limited by the transmission of the optical elements, in particular of the glass fibers used.

The laser system of the present invention is particular advantageous if it comprises at least one stabilizer for stabilizing the frequency comb onto a certain offset frequency ($f_0$) and/or onto a certain mode distance ($\Delta f$), since the modes of the comb are then fixed and known with absolute certainty; and the knowledge of the mode position is transferred onto the modes of the spectrally shifted comb due to the full preservation of coherence.

It is preferred that the optical amplifier comprises an optically pumped, erbium and/or ytterbium doped optical fiber. Such an amplifier is compact, robust, and easily controllable in its amplification factor.

The pump source for the amplifier may be one (or several) diode laser(s). They have a long life and require minimal maintenance.

If a diode laser is provided as a pump source for the amplifier, the amplification factor of the amplifier may be controlled in a simple way via the current at the diode laser. In particular, the amplification factor may then be controlled continuously.

In a preferred variant of the invention, the amplifier already generates a first Raman shift of the frequency comb before the Raman medium. Due to the dual Raman shift (in the amplifier and subsequently in the Raman medium), the extent of the complete frequency shift is increased. The contribution of the amplifier to the Raman shift may, for example, be in the range of 10 to 30 nm.

Preferably, the Raman medium comprises an optical fiber, in particular a polarization preserving fiber. The fiber has the advantage of merely requiring limited space in the laser system. Further, the Raman shift generated by the fiber increases with the length of the fiber. Hence, the length of the fiber may be used for a coarse tuning of the Raman shift, while the fine-tuning is achieved via the amplification factor of the amplifier.

It is particularly convenient if the Raman medium or an optical fiber used as the Raman medium is connected by a splice connection with an optical fiber of the amplifier. Since the splicing occurs already before installing the elements in the laser system, the amplifier and the Raman medium do not have to be aligned or adjusted to each other anymore in the laser system. Also, during operation of the laser system, they may never lose their alignment, such that the laser system requires less maintenance.

The laser system of the present invention offers particular advantages in an embodiment in which the Raman medium is followed by a frequency selective attenuator. At first sight this may seem disadvantageous, since most applications require an output power as high as possible. As already explained, in the inventive laser system the degree of the Raman shift of the frequency comb may be varied by a variation of the amplification power. This means that the larger the central wavelength of comb, the higher is the output power of the laser system. For some applications it may now be advantageous if the output power of the laser system is at least substantially independent of the central wavelength of the comb. In particular, when investigating sensitive, for example biological, samples with the frequency comb, the sample might be negatively influenced or even destroyed if the incident light power becomes too strong. And in applications at which the central wavelength is increased or decreased once or several times in a ramp-like fashion, i.e. when scanning over the available spectrum, a periodic variation of the laser power may not be desired.

With a frequency selective attenuator a variation in output power may be suppressed. In this connection, it is particular advantageous if the degree of attenuation of the attenuator increases towards lower frequencies, and further if the change of attenuation per frequency interval is correlated as closely as possible with the variation of laser power in front of the attenuator. If, for example, the laser power in front of the attenuator linearly increases with decreasing frequency, it would be advantageous if also the degree of attenuation of the attenuator increases linearly with decreasing frequency. In this way, the output power of the laser system may be stabilized.

It is conceivable that the attenuator is an "active" element, the attenuation degree of which may be varied by an actuator in a synchronous way to varying the amplification factor of the amplifier. However, this requires a considerable feedback effort, and without a very precise synchronization fluctuations in output power are still possible. Therefore, it is preferred that the attenuator is a "passive" element that does not require a controllable actuator. Its attenuation characteristics should then be chosen in advance in adaptation to the preceding amplifier, such that a variation of output power due to a variation of the amplification factor and a corresponding frequency shift is compensated to the best possible degree. In this way, the output power always remains constant, even if the frequency comb is shifted. If desired, the attenuator could certainly also be configured such that the output power of the laser system does not remain constant, but changes with a predetermined rate per frequency interval of the Raman shift.

A simple embodiment of a "passive" attenuator may be realized by the attenuator comprising a mirror, the reflectivity or transmissivity of which (depending on the orientation of the mirror) increases or decreases towards lower frequencies. Such a mirror may be a dichroic mirror.

In a different embodiment of a "passive" attenuator, the attenuator comprises an optical fiber that has frequency dependent losses. This embodiment has the additional advantage of facilitating manufacturing and alignment.

The frequency dependent losses in the optical fiber may be achieved by the fiber being doped with certain absorbers. However, absorption would have the disadvantage of the temperature of the fiber increasing. In a simpler and better embodiment, the fiber is wound with a comparably small radius of curvature. In the curved portions, higher frequency components are guided better in the fiber, while the loss increases for lower frequency components. Since the losses are not due to absorption, the temperature of the fiber does not increase in this embodiment.

Depending on the desired magnitude of attenuation, and depending on the characteristics of the unit of amplifier and Raman medium, the radius of curvature of the optical fiber could—at least in portions of the fiber—be 15 to 100 millimeters, in particular 25 to 40 millimeters. The length of the fiber could be between 0.5 and 50 meters.

In a particularly convenient embodiment, the degree of attenuation of the attenuator per frequency interval is variable, in order to be able to adapt the attenuation characteristics to a different environment or different experimental requirements.

For this purpose, for example, the radius of curvature of the optical fiber might be variably adjustable. This could be put into practice by providing a cylindrical coil or reel comprising a plurality of cylinder segments, onto which the fiber is wound. If the cylinder segments are radially moved outwards in relation to the cylinder axis, the radius of curvature of the fiber is increased. If, on the other hand, the cylinder segments are radially moved towards the cylinder axis, and the fiber simultaneously is subject to a certain tension, the radius of curvature of the fiber is decreased, and the variation of the degree of attenuation per frequency interval increases. In a different embodiment, a fiber segment is wound in a circular fashion onto two jaws. If the jaws are moved relative to another, the circular winding is deformed into an ellipse, leading to a change in the fiber's radius of curvature.

If the attenuator is realized by means of an optical fiber, this fiber may advantageously be connected with an optical fiber of the Raman medium by a splice connection. Since the splice connection may be already provided before installing the elements into the laser system, the attenuator and the Raman medium do not have to be aligned or adjusted to each other anymore in the laser system. Further, during operation of the laser system they can never lose their mutual alignment, such that the maintenance requirements of the laser system are decreased. The laser system becomes particularly simple and easy to maintain if both the amplifier and the Raman medium, as well as the Raman medium and the attenuator are connected to each other via splice connections.

In order to be able to transfer the frequency comb to even further frequency ranges, the Raman medium and/or, if present, the attenuator could be followed by a frequency conversion, for example by a frequency doubling element. By means of this conversion, the frequency comb could be transferred to a central wavelength between approximately 800 and 1100 nanometers, while still maintaining all coherence properties of the comb. For example, a BBO crystal (beta barium borate) or a periodically poled lithium niobate crystal (PPLN) are suitable as a frequency doubling element. The differently poled areas of the crystal could be provided for in the shape of parallel layers in the crystal, or in a fan-like pattern.

Preferred values for the repetition rate of the frequency comb generator are between (and including) 80 and 500 MHz, preferably between 150 and 300 MHz or even higher. A high repetition rate, which may be realized by a "short" resonator of the oscillator, has the advantage of a large mode spacing Δf, such that the single modes may be easily spectrally separated from each other. However, there is also another advantage; at pulse energies of 0.1 to 0.2 nanojoule (nJ) the amplification in the optical amplifier is particularly efficient. At pulse energies between 1 to 3 nanojoules (nJ) the Raman shift is particularly efficient. A high repetition rate allows to increase the mean output power of the laser system while maintaining moderate pulse energies and, thus, an efficient amplification and frequency shifting.

In a variation of the invention, the Raman medium comprises a plurality of Raman media, and the optical properties of one Raman medium are different from another Raman medium. This allows to adapt each Raman medium as perfectly as possible to the light entering into the respective Raman medium, in order to increase the efficiency of the Raman shift. For example, the first Raman medium entered by the frequency comb may be configured to have a maximum efficiency with respect to the Raman shift at the central frequency of the original frequency comb, leading to a Raman frequency shift of the comb of $-\Box f_{shift1}$. Each subsequent Raman medium may then be configured to have its maximum efficiency with respect to the Raman shift at a frequency which corresponds to the central frequency of the frequency comb shifted by the preceding Raman medium, i.e. the second Raman medium has its maximum efficiency at the original central frequency minus $\Box f_{shift1}$.

In a preferred configuration of this embodiment, the Raman medium comprises a plurality of optical fibers; and the optical properties of one fiber are different from another fiber.

For example, the different Raman fibers may be different in their nonlinear optical properties or in their dispersion properties.

For the sake of stability and ease of maintenance, the fiber sections may be spliced to each other.

It is also conceivable to configure the plurality of fiber sections such that they are different in the cross sectional area of their cores. A smaller core will lead to higher light intensities and, thus, higher nonlinear optical properties.

For example, three sections of Raman fibers may be spliced together, the section to be entered first by the frequency comb having the largest core diameter, the second fiber having a smaller core diameter, and the third fiber section having the smallest core diameter, in order to achieve a very effective Raman shift over several 100 nm.

In addition to the laser system, the invention is also concerned with the application of the frequency comb generated by the inventive laser system for measuring an optical frequency, for generating optical reference frequencies, as an optical clock, as well as using the frequency comb in telecommunication or in microscopy, in particular in fluorescence microscopy or in two-photon-microscopy.

DESCRIPTION OF DRAWINGS AND PREFERRED EMBODIMENT

In the following, a preferred embodiment and best mode of the invention will be described with reference to the attached drawing. In particular, FIG. 1 is a schematical view of a preferred embodiment of the laser system according to the present invention, and FIG. 2 is a diagram showing the frequency comb at different positions in the laser system of the present invention.

DETAILED DESCRIPTION

Figure 2:
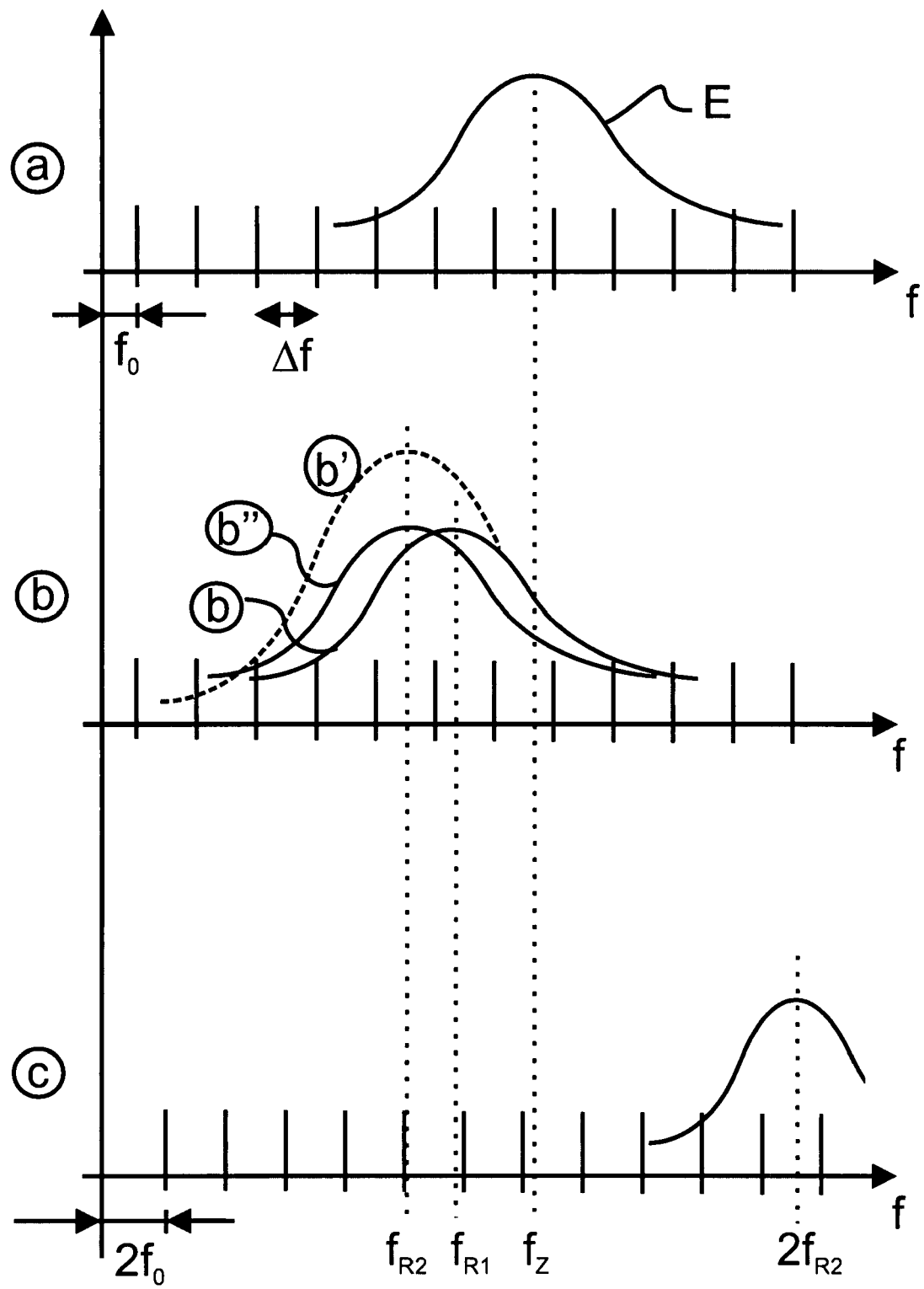

FIG. 1 is a schematical view of a laser system 1 according to the present invention. Starting point of the laser system is a frequency comb generator 2 for generating a frequency comb of optical frequencies with an offset frequency $f_0$ and a plurality of equidistant nodes $f_n = f_0 + n \Delta f$. The frequency comb generator 2 or oscillator may be a diode pumped ultra short pulse fiber laser, for example a femtosecond $Er^+$ fiber laser with a central wavelength of approximately 1550 nm. The repetition rate of the oscillator and, thus, the mode spacing Δf, may be set to a value of, for example, 100 MHz or 200 MHz. The frequency comb coupled out of the frequency comb generator 2 at the position (a) is schematically shown in the first "line" in FIG. 2. It is constituted by the equidistant modes, the amplitudes of which are determined by an envelope E.

A beam splitter 3 divides the frequency comb into a first portion that is later routed to an exit or output 4 of the laser system 1, and a second portion that is guided to one or several stabilizers 5. As known from DE 199 11 193 A1, EP 1 161 782 B1, or DE 100 44 404 C2, the stabilizer(s) 5 is/are configured to stabilize the frequency comb onto a certain, predetermined offset frequency $f_0$ and/or a predetermined mode spacing Δf, for example by comparison with an external, known reference frequency. For this purpose, the stabilizer 5 may comprise an additional amplification of the optical signal and a spectral broadening by non-linear optical elements into an optical octave, as described in DE 199 11 193 A1, EP 1 161 782 B1, and DE 100 44 404 C2. A feedback is achieved via one or several actuators 6 such that the frequency comb generator 2 may be set and controlled onto the desired offset frequency $f_0$ and/or the desired mode distance Δf. For details of this absolute stabilization of the frequency comb, reference is made to DE 199 11 193 A1, EP 1 161 782 B1, and DE 100 44 404 C2, the entire content of which is herein incorporated by reference.

The portion of the frequency comb intended to be routed towards the exit 4 of the laser system 1 enters into an optical amplifier 7. At the entry into the amplifier 7, the energy of a single laser pulse is about 0.1 nJ, since at such a pulse energy the amplification is particularly efficient. At a repetition rate of 100 MHz, this corresponds to a mean laser power of 10 mW; at a repetition rate of 200 MHz, this corresponds to a mean laser power of 20 mW.

An optical fiber doped with erbium and/or ytterbium ions and optically pumped by a diode laser (not shown) is preferably used as the amplifier 7. The amplification factor, by which the amplitudes of the frequency comb are amplified, is variably controllable by varying the current on the diode laser(s). The fiber of the amplifier 7 generates a first Stokes-Raman shift of the frequency comb in a magnitude of 10 to 20 nm.

Subsequent to the amplifier 7, the frequency combs pass a Raman medium 8, which may be a polarization preserving fiber spliced to the fiber of the amplifier 7. The Raman medium 8 induces a strong Stokes-Raman shift of the frequency comb of a magnitude of 40 to 600 nm, i.e. to wavelengths of 2.0 micrometers or even 2.2 micrometers. The polarization preserving fiber is configured such that after a short distance a soliton is generated from the laser pulse. The "soliton self-frequency shift" in the Raman medium 8 leads to a frequency shift of the soliton. The longer the optical path in the Raman medium 8 and the higher the amplitudes of the frequency comb passing through the Raman medium 8, the larger the frequency shift is. Thus, the length of the fiber may be used as a coarse tuning of the generated Raman shift, while the fine tuning consecutively may be performed by the amplification factor of the amplifier 7. A variable tuning by varying the amplification factor (e.g. via the pump power at the amplifier 7) is possible over several 100 nm.

At this point, i.e. immediately behind the Raman medium 8, the frequency shifted comb, which is still stabilized onto the original offset frequency $f_0$ and/or the original mode spacing $\Delta f$, may directly be routed to an exit 4' of the laser system 1. This would provide a laser system 1 which may generate frequency tunable, stabilized frequency combs, the central wavelengths of which are variable between 1550 nm and 2.2 micrometers while fully maintaining their coherence.

In the preferred embodiment shown in FIG. 1, however, the Raman medium 8 is followed by an (optional) attenuator 9, the attenuation degree of which is frequency dependent and increases towards lower frequencies. In the preferred embodiment, the attenuator 9 is an optical fiber spliced onto the fiber of the Raman medium 8 and being wound onto a coil with a comparatively small radius of curvature of approximately three centimeters. The lower the frequency of a mode, the higher is its loss in the attenuator 9. The frequency dependent degree of attenuation of the attenuator 9 is controlled by the curvature of the fiber such that an increase in power generating a Raman shift is compensated as closely as possible, such that irrespective of the degree of the Raman shift a constant mean power is available behind the attenuator 9. A frequency scan could now be performed by continuously changing the amplification factor of the amplifier 7 without changing the output power of the laser system 1.

As a further optional element a frequency doubler 10 may be provided as a frequency converter in the laser system 1, in order to frequency double the modes of the frequency comb. The frequency doubler 10 may be provided with or without a preceding attenuator 9. The doubler 10 may be a BBO or a PPLN crystal, by means of which the central wavelength of the laser pulses constituting the frequency comb may be divided to approximately 800 nm to 1100 nm, depending on the preceding Raman shift. At the frequency doubling, the offset frequency is also doubled from $f_0$ to $2f_0$. A doubling of the mode spacing $\Delta f$, however, which may be expected mathematically, does not occur. Rather, the mode spacing and the pulse repetition rate are maintained. The corresponding modes of the new frequency comb are generated by sum frequency generation from the modes of the original comb. If the original frequency comb is stabilized onto an offset frequency of $f_0$, the frequency doubled comb is automatically stabilized onto an offset frequency of $2f_0$, i.e. frequency stability and coherence are not impaired. In this case, it can be particularly advantageous to adapt the attenuator 9 such that it counteracts a varying efficiency of the harmonic generation depending on frequency.

Further, the laser system may comprise a second frequency doubling step, which operates mutatis mutandis under conditions similar to the first step. Alternatively, a different frequency conversion step may be available that relies on sum or difference frequency generation.

At the exit 4 of the laser system 1 a frequency comb shifted to longer wavelengths or (after frequency conversion) to the visible or near infrared spectral region is now available, which is exactly as coherent and frequency stabilized as the original comb generated in the frequency comb generator. By making further, new spectral ranges accessible for frequency stabilized combs of sufficient power, the laser system 1 of the present invention enables a plurality of unique novel applications. The radiation at the exit 4 of the laser system 1 may be surveyed via suitable detectors, such as photodiodes or photomultipliers 11, a power meter or a (grating) spectrometer. It is also conceivable to install a feedback to the frequency comb generator 2 via a suitable feedback circuit.

The shift of the frequency comb is schematically shown in FIG. 2. FIG. 1 explains at which positions within the laser system 1 the frequency combs shown in FIG. 2 are present. The first "line" in FIG. 2 shows the frequency comb coupled out of the frequency comb generator 2 at the position (a). This comb is constituted of the equidistant modes $f_n = f_0$ to n $\Delta f$, the respective amplitudes of which are determined by an envelope E. The comb has its highest amplitude at a "central frequency $f_z$", corresponding to the central wavelength (e.g. 1550 nm).

At a first lower amplification factor of the amplifier 7, shown in situation (b), the maximum of the envelope function E is shifted by the Raman medium 8 to a lower frequency $f_{R1}$, but the offset frequency $f_0$ and the mode spacing $\Delta f$ are maintained. At a higher amplification factor—situation (b') shown in broken lines—the magnitude of the Raman shift increases, such that the maximum of the envelope E is shifted to an even lower frequency $f_{R2}$. Due to the higher amplification factor, however, the amplitude of the envelope E is also increased.

If an attenuator 9 is present in the laser system 1 and its frequency dependent attenuation degree is configured such that an increase in intensity for the purpose of a larger Raman shift is exactly compensated, the frequency comb after passing the attenuator 9 has an envelope designated with (b"). This new envelope assumes its maximum also approximately at the frequency $f_{R2}$, but its amplitude now corresponds to the situation (b) with the lower amplification factor. Hence, by the mutual adaptation of the amplifier 7, of the Raman medium 8, and of the attenuator 9, it is possible to tunably shift the frequency comb over a very large frequency range while maintaining its amplitude, i.e. while maintaining a constant mean laser power. If the laser system 1 is also equipped with a frequency doubler 10, the frequency comb or the envelope E will be shifted to a new, higher central frequency $2f_{R1}$, or $2f_{R2}$, depending on the amplification factor of the amplifier 7. This situation (c) at the exit 4 of the laser system 1 of FIG. 1 is depicted in the third "line" in FIG. 2. Due to the doubling of all frequencies of the comb, the offset frequency is also doubled to $2f_0$.

Starting from the described embodiment, the laser system of the present invention may be amended in several ways. For example, an Ytterbium doped fiber laser with a central wavelength of 1030 nm may me used as the frequency comb generator instead of the Erbium doped fiber laser. As explained, the laser system may be put into practice without the attenuator 9 or the frequency doubler 10, or it may only have one of these two elements. A different short pulse or ultra short pulse laser, such as a Kerr lens mode locked titan sapphire laser, which is known as such, may be used as a frequency comb generator. Further, no stabilizer, or one or several stabilizers 5, may be provided for stabilizing the degrees of freedom of the generated frequency comb. A plurality of suitable elements may also be used as the optical amplifier 7 and the Raman medium 8. The amplifier 7 should be equipped with control elements in order to manually or electronically control the amplification factor. If the laser system 1 is designed for a certain application, at which only a single, predetermined position of the frequency comb is necessary, the amplifier 7 could also be set onto a fixed amplification factor, at which the desired Raman shift is continuously generated. The amplification factor would then no longer be variable anymore. It is also conceivable to use a mode of the frequency doubled comb at the exit 4 of the laser system 1 for stabilizing the frequency comb generator 2 by guiding this mode into the stabilizer 5.

While only preferred embodiments of the invention are described herein in detail, the invention is not limited thereby. It is believed that the advantages and improved results of the invention will be apparent from the foregoing description. It will be apparent that various changes and modifications can be made without departing from the spirit and scope of the invention as sought to be defined in the following claims.

The invention claimed is:

1. A laser system comprising:
a frequency comb generator for generating a frequency comb of optical frequencies with an offset frequency and a plurality of equidistant modes;
an optical amplifier for amplifying the frequency comb coupled out of the frequency comb generator;
a Raman medium provided after the amplifier and adapted for generating a Raman shift of the frequency comb, the Raman medium being configured such that a soliton is generated from the frequency comb and a soliton self-frequency shift in the Raman medium leads to a frequency shift of the soliton; and
a frequency dependent attenuator arranged downstream of the Raman medium, an attenuation degree of the attenuator being configured such that a constant mean laser power is provided behind the attenuator irrespective of the degree of the Raman shift,
wherein an amplification factor of the amplifier is variable.

2. Laser system according to claim 1 further comprising at least one stabilizer for stabilizing the frequency comb onto a predetermined offset frequency or onto a pre-determined mode spacing.

3. Laser system according to claim 1, wherein the optical amplifier comprises an optically pumped, ion doped optical fiber.

4. Laser system according to claim 1 further comprising a diode laser as a pump source for the amplifier.

5. Laser system according to claim 4, wherein the amplification factor of the amplifier is controllable via the current at the diode laser.

6. Laser system according to claim 1, wherein the amplifier generates a first Raman shift of the frequency comb before the Raman medium.

7. Laser system according to claim 1, wherein the Raman medium comprises an optical fiber.

8. Laser system according to claim 7, wherein the optical fiber is polarization preserving.

9. Laser system according to claim 1, wherein the Raman medium is connected to an optical fiber of the amplifier by means of a splice connection.

10. Laser system according to claim 1, wherein the attenuation degree of the attenuator increases towards lower frequencies.

11. Laser system according to claim 1, wherein the attenuation degree of the attenuator linearly increases towards lower frequencies.

12. Laser system according to claim 1, wherein the attenuator is a passive element.

13. Laser system according to claim 1, wherein the attenuator comprises a mirror, the reflectivity of which increases or decreases towards lower frequencies.

14. Laser system according to claim 1, wherein the attenuator comprises a mirror, the transmissivity of which increases or decreases towards lower frequencies.

15. Laser system according to claim 1, wherein the attenuator comprises an optical fiber.

16. Laser system according to claim 15, wherein the optical fiber is arranged with a curvature.

17. Laser system according to claim 15, wherein a radius of curvature of the optical fiber at least in portions of the fiber has a value of 15 to 100 millimeters.

18. Laser system according to claim 15, wherein the attenuation degree of the attenuator per frequency interval is variable.

19. Laser system according to claim 15, wherein the radius of curvature of the optical fiber is variably adjustable.

20. Laser system according to claim 15, wherein an optical fiber of the amplifier is connected to an optical fiber of the Raman medium by means of a splice connection.

21. Laser system according to claim 1, further comprising a frequency converter.

22. Laser system according to claim 1, wherein the repetition rate of the frequency comb generator is between 80 and 500 MHz.

23. Laser system according to claim 1, wherein the repetition rate of the frequency comb generator is between 150 and 300 MHz.

24. Laser system according to claim 1, wherein the Raman medium comprises a plurality of Raman media, and the optical properties of one Raman medium are different from the optical properties of another Raman medium.

25. Laser system according to claim 1, wherein the Raman medium comprises a plurality of optical fibers, and the optical properties of one fiber are different from the optical properties of another fiber.

26. Laser system according to claim 25, wherein the fibers are different in their nonlinear optical properties or in their dispersion properties.

27. Laser system according to claim 25, wherein the fibers are spliced to each other.

28. Laser system according to claim 25, wherein the fibers are different in the cross sectional area of their cores.

29. Laser system according to claim 1, wherein the frequency comb is used for measuring the optical frequencies.

30. Laser system according to claim 1, wherein the frequency comb is used for generating an optical reference frequency.

31. Laser system according to claim 1, wherein the frequency comb is used in an optical clock.

32. Laser system according to claim 1, wherein the frequency comb is used for comparing two optical frequencies.

33. Laser system according to claim 1, wherein the frequency comb is used in the field of telecommunication.

34. Laser system according to claim 1, wherein the frequency comb is used in the field of microscopy.

35. Laser system according to claim 15, wherein a radius of curvature of the optical fiber at least in portions of the fiber has a value of 25 to 40 millimeters.

* * * * *